United States Patent [19]
Cabri et al.

[11] Patent Number: 5,304,641
[45] Date of Patent: Apr. 19, 1994

[54] PROCESS FOR THE SYNTHESIS OF EXOMETHYLENECEPHAMS

[75] Inventors: Walter Cabri, Rozzano; Ilaria Candiani, Busto Arsizio; Angelo Bedeschi, Milan, all of Italy

[73] Assignee: Farmitalia Carlo Erba S.r.l., Milan, Italy

[21] Appl. No.: 21,174

[22] Filed: Feb. 16, 1993

[30] Foreign Application Priority Data

Feb. 17, 1992 [GB] United Kingdom ............ 9203327

[51] Int. Cl.$^5$ ............................................ C07D 501/02
[52] U.S. Cl. ............................................ 540/215; 540/228; 540/230
[58] Field of Search ..................... 540/230, 215, 228

[56] References Cited

U.S. PATENT DOCUMENTS

| | | | |
|---|---|---|---|
| 3,929,775 | 12/1975 | Ochiai et al. | 540/230 |
| 4,354,022 | 10/1982 | Takaya et al. | |
| 5,126,446 | 6/1992 | Brown et al. | 540/215 |

FOREIGN PATENT DOCUMENTS

| | | |
|---|---|---|
| 0132394 | 1/1985 | European Pat. Off. |
| 0341694 | 11/1989 | European Pat. Off. |
| 2213287 | 8/1974 | France |

OTHER PUBLICATIONS

Chemical Abstracts, vol. 105, No. 13, Sep. 29, 1986, AN-114837v, p. 656, JP-A-6 153 289.

Chemical Abstracts, vol. 97, No. 17, Oct. 25, 1982, AN-144674y, p. 668, JP-A-8 270 893.

*Primary Examiner*—Nicolas S. Rizzo
*Attorney, Agent, or Firm*—Oblon, Spivak, McClelland, Maier & Neustadt

[57] ABSTRACT

The present invention relates to a process for the preparation of exomethylene cephams, which are useful intermediates in the production of many useful β-lactam antibiotics.

More particularly there is provided a process for preparing a compound of formula I

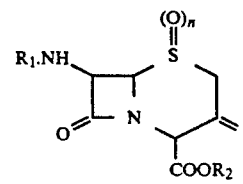

wherein n is 0 or 1, $R_1$ is hydrogen atom or an organic residue and $R_2$ is a carboxy protecting group, which process comprises reacting a compound of the formula II

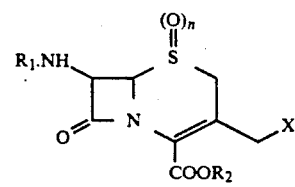

wherein X is halogen atom or acetoxy group and $R_1$ n and $R_2$ are as defined above with a lanthanide complex.

5 Claims, No Drawings

PROCESS FOR THE SYNTHESIS OF EXOMETHYLENECEPHAMS

The present invention relates to a process for the preparation of exomethylene cephams, which are useful intermediates in the production of many useful β-lactam antibiotics.

Few methods are known for the transformation of cephem derivatives into exomethylene cephams. These methods require the use of dangerous and toxic Cr(II) derivatives (J. Chem. Soc., Chem. Commun, 1972, 800), or the use of the expensive electrochemical reduction (Torii et al., Bull. Chem. Soc. Jpn., 59, 3975, 1986) starting from 3-acetoxymethyl or 3-halomethylcephem, respectively. There are other methodologies which utilize Zn as reducing agent, but starting from more expensive 3' thiofunctionalized cephem derivatives (see for instance "Chemistry and Biology of b-lactam Antibiotics, Vol. 1, p. 101, Morin and Gormann Ed., Academic Press, 1982), and/or with the use of huge amounts of the metal (typically more of 2.5/1 by weight of substrates in solvents such as DMF), which implies the necessity of long and tedious purification processes. Moreover the overall yields of such processes are quite low, the exomethylene compounds are in fact often obtained in mixture with the corresponding cephems. The present invention provides a process for preparing a compound of formula I

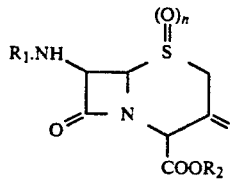

wherein n is O or 1, $R_1$ is hydrogen atom or an organic residue and $R_2$ is a carboxy protecting group, by reacting a compound of the formula II

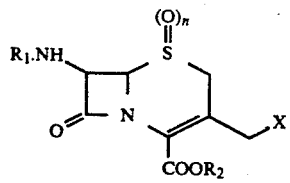

wherein X is halogen atom or acetoxy group and n, $R_1$ and $R_2$ are as defined above with a lanthanide complex. Preferably the process of the present invention includes reacting a compound of formula II, wherein $R_1$, $R_2$ and X are as defined above, in a suitable solvent with up to 4 molar equivalents of a lanthanide complex, for example from 0.1 to 4 molar equivalents of a lanthanide complex, at a temperature of from −110° C. to the solvent reflux temperature, preferably from −78° C. to room temperature for a period of from a few minutes to one day, for example from two minutes to one day, preferably for a few hours, for example from 0.5 to 4 hours, and then quenching the reaction mixture with a protic agent. Preferred lanthanide complexes operating the aforementioned conversion are samarium and ytterbium complexes. The ligands of the above mentioned complexes may be inorganic such as halogenides or organic such as cyclopentadienyl or acetates.

The lanthanide complexes, for example the samarium and ytterbium complexes, may be used as such or optionally prepared from the corresponding metals, according to known methodologies. The lanthanides may be optionally recycled, for instance, through reduction by known methods. The lanthanide complexes, for example the samarium and ytterbium complexes may be optionally used in catalytic amounts, provided that a co-reducing agent is present in the reaction medium or by reductive electrochemical methods (see for instance J. Chem. Soc., Chem. Commun., 1989, 276).

Suitable solvents are organic solvents, preferred examples are THF, dimethoxyethane, toluene, HMPA (hexamethylphosphoric triamide), acetonitrile, or a mixture thereof. Suitable protic agents are, for instance, water and alcohols, the preferred ones being water, methanol, ethanol, propanol, i-propanol, butanol, and t-butanol. Preferably n is O.

The organic residue which $R_1$ may represent comprise a linear or branched $C_1$-$C_5$ alkanoyl group; a benzoyl group, in which the phenyl ring is optionally substituted by one or more substituents chosen from:
 i) $C_1$-$C_4$ linear or branched alkyl group,
 ii) $NO_2$,
 iii) $C_1$-$C_4$ linear or branched alkoxyl group,
 iv) an halogen atom;

an optionally substituted, as defined above, phenyl-(linear or branched)-$C_2$-$C_4$-alkanoyl group, an optionally substituted, as defined above, phenoxy-(linear or branched)-$C_2$-$C_4$-alkanoyl group; a phthalimido group; a linear or branched $C_6$-$C_{10}$thienylalkanoyl group; or a linear or branched $C_4$-$C_8$ (1,3,4-thiodiazolyl)thioalkanoyl residue; a linear or branched $C_1$-$C_4$ alkoxycarbonyl group; an optionally substituted, as defined above, phenoxycarbonyl group; an optionally substituted, as defined above, phenyl-(linear or branched)-$C_1$-$C_4$-alkoxycarbonyl group; a $C_1$-$C_4$ trihaloalkoxy carbonyl group. The carboxy protecting group which $R_2$ represents is preferably chosen from linear or branched $C_1$-$C_4$ alkyl, a linear or branched $C_1$-$C_4$ trihaloalkyl group, an optionally substituted, as defined above, benzyl, a trialkylsilyl, an optionally substituted, as defined above, diphenyl methyl, or a linear or branched $C_2$-$C_4$ alkenyl group. Preferably, $R_1$ is H; a linear or branched $C_1$-$C_5$ alkanoyl group, and more preferably a formyl, acetyl, or pivaloyl group; a benzoyl group, in which the phenyl ring is optionally substituted by a $NO_2$, or OMe group, and more preferably an unsubstituted benzoyl group; an optionally substituted, as defined above, phenyl-(linear or branched)-$C_2$-$C_4$-alkanoyl group, and more preferably a phenylacetyl group; an optionally substituted, as defined above, phenyloxy-(linear or branched)-$C_2$-$C_4$-alkanoyl group, and preferably a phenoxyacetyl group; a linear or branched $C_1$-$C_4$ alkoxycarbonyl group, and more preferably an ethoxy, or a t-butoxycarbonyl group; an optionally substituted, as defined above, phenoxycarbonyl group, more preferably an unsubstituted phenoxycarbonyl group; an optionally substituted, as defined above, phenyl-(linear or branched)-$C_1$-$C_4$-alkyloxycarbonyl group, more preferably a p-$NO_2$ or a pMeO benzyloxycarbonyl group; a $C_2$-$C_4$ trichloroalkoxycarbonyl group, more preferably a 2,2,2 trichloroethoxycarbonyl group. Preferred $R_2$ are chosen from linear or branched $C_1$-$C_4$ alkyl, more preferably methyl, ethyl, or t-butyl; a benzhydryl group; a trihaloalkyl group, preferably 2,2,2 trichloroethyl.

Among the benzyl groups, benzyl, p-nitrobenzyl, and p-methoxybenzyl groups are preferred. A trialkylsilyl group means preferably a trimethylsilyl, or a t-butyldimethylsilyl group. Among the optionally substituted benzhydryl groups, the benzhydryl group is preferred. Preferred halogens are chlorine, bromine and iodine atoms. Optical isomers having all possible stereochemistries at positions 4, 6, and 7 in formula (II) are embraced within the present invention, either as single isomers or mixtures thereof, the preferred ones being the 6(R), 7(R) isomers, i.e. the "natural", as indicated in the above mentioned Chemistry and Biology of b-Lactam Antibiotics, p. 95, configuration products. The starting materials of formula II are known and may be prepared according known methodologies. Due to the mild and easy reaction condition, and to the high yields and selectivity observed in the reaction, the method of the present invention can be particularly useful for the preparation of compounds of formula I, in large scale. As stated above, the compounds of the formula I are useful intermediates for the preparation of β-lactam antibiotics, as for example described in the above mentioned Chemistry and Biology of β-Lactam Antibiotics, p. 96.

The compound of formula (I) may therefore be converted into a β-lactam antibiotic, for example of the following formula (Ia):

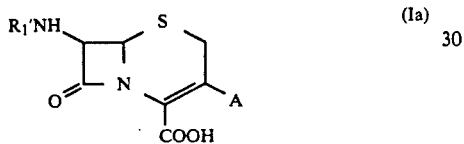

wherein:
$R_1'$ is an aminophenylacetyl, 2-(2-amino-4-thiazolyl)-4-carboxy-1-oxo-2-butenyl or 2-amino-4-thiazolyl(methoxyimino)-acetyl group, and A is a halogen, $C_1$-$C_4$ alkoxy group or hydrogen; or a pharmaceutically acceptable salt thereof.

When A is a halogen it is typically chlorine. When A is a $C_1$-$C_4$ alkoxy group it is typically a methoxy group.

The conversion of a compound of formula (I) into a compound of formula (Ia) is carried out by performing conventional reactions well known in the chemistry of β-lactam antibiotics: for example, the conversion typically comprises removing the carboxy protecting group $R_2$ as defined above, substituting the group $R_1$ as defined above by an acylating group $R^1$, as defined above, and converting the exomethylene group into the desired A group. The resulting compound (Ia) may then, if desired, be converted into a pharmaceutically acceptable salt thereof.

The β-lactam antibiotic of formula (Ia), or the pharmaceutically acceptable salt thereof, may then be formulated together with a pharmaceutically acceptable carrier or diluent. The resulting pharmaceutical composition may be for oral or parenteral administration.

The following examples illustrates, but not limit the above mentioned process.

Example 1

Methyl 7β-benzoylamino-3-methylenecepham-4carboxylate

To 48 ml of a solution of $SmI_2$ in THF (0.1M) a solution of 1 g of methyl 7β-benzoylamino-3-iodomethyl-3-cephem-4carboxylate in 100 ml of dry THF, was added by dropping at $-78°$ C. The resulting mixture was allowed to warm to room temperature in 0.5 hours. Water was added, and the mixture stirred for further 0.2 hours at room temperature. Methylene chloride was added, and the organic phase was separated, washed with brine, dried, and evaporated in vacuo. After column chromatography the title product was isolated in 65% yield.

NMR (CDCl$_3$) δ ppm: 3.21 and 3.76 (2H, two d, J=14 Hz), 3.83 (3H, s), 5.13 (1H, s), 5.23 (1H, br s), 5.25 (1H, s), 5.48 (1H, d, J=4.5 Hz), 5.85 (1H, dd, J=4.5 and 9 Hz), 6.93 (1H, d, J=9 Hz), 7.35–7.85 (5H, m), Mass (FD, m/e): 332 (M). By analogy the following compounds were prepared, starting from the corresponding iodides:

t-Butyl 7β-benzoylamino-3-methylenecepham-4carboxylate.

2,2,2 trichloroethyl 7β-benzoylamino-3-methylenecepham-4-carboxylate.

Benzyl 7β-benzoylamino-3-methylenecepham-4-carboxylate.

p-Methoxybenzyl 7β-benzoylamino-3-methylenecepham-4carboxylate.

p-Nitrobenzyl 7β-benzoylamino-3-methylenecepham-4carboxylate.

Benzidryl 7β-benzoylamino-3-methylenecepham-4carboxylate.

Example 2

Methyl 7β-benzoylamino-3-methylenecepham-4carboxylate

To a solution of 48 ml of $SmI_2$ in THF (0.1M), a solution of 0.8 g of methyl 7β-benzoylamino-3chloromethyl-3-cephem -4-carboxylate in 100 ml of dry THF, was added by dropping at $-78°$ C. The resulting mixture was allowed to warm to room temperature in 0.5 hours. Water was added, and the mixture stirred for further 0.2 hours at room temperature. After the usual work-up and column chromatography, the title product was isolated in 96% yield.

By analogy the following compounds were prepared, starting from the corresponding chlorides:

t-Butyl 7β-t-butyloxycarbonylamino-3-methylenecepham-4carboxylate.

2,2,2 trichloroethy 7β-t-butyloxycarbonylamino-3-methylenecepham-4-carboxylate.

Benzyl 7β-t-butyloxycarbonylamino-3-methylenecepham -4carboxylate.

p-Methoxybenzyl 7β-butyloxycarbonylamino-3-methylenecepham -4-carboxylate.

p-Nitrobenzyl 7β-butyloxycarbonylamino-3-methylenecepham -4-carboxylate.

Benzidryl 7β-butyloxycarbonylamino-3-methylenecepham-4carboxylate.

Example 3

Methyl 7β-benzoylamino-3-methylenecepham-4carboxylate

The reaction was carried out as described in example 1, except that methyl 7β-benzoylamino-3-bromomethyl-3-cephem-4carboxylate was used instead as starting material. The title compound was isolated in 70% yield. By analogy the following compounds were prepared, starting from the corresponding bromides:

t-Butyl 7β-acetylamino-3-methylenecepham-4carboxylate.

2,2,2 trichloroethyl 7β-acetylamino-3-methylenecepham -4-carboxylate.

Benzyl 7β-acetylamino-3-methylenecepham-4-carboxylate.

p-Methoxybenzyl 7β-acetylamino-3-methylenecepham-4-carboxylate.

p-Nitrobenzyl 7β-acetylamino-3-methylenecepham-4-carboxylate.

Benzidryl 7β-acetylamino-3-methylenecepham-4-carboxylate.

Example 4

The reaction was carried out as described in example 1, except that t-buOH was added at −78° C. The reaction was let warm at room temperature. After the usual work up, the desired product was obtained in 60% yield.

Example 5

The reaction was carried out as described in example 1, except that YbI$_2$ was used. The title compound was isolated in 41% yield.

Example 6 p-Methoxybenzyl 7β-phenoxyacetylamino-3-methylenecepham-4-carboxylate

To a solution of 48 ml of SmI$_2$ in THF (0.1M), a solution of 1.1 g of p-methoxybenzyl 7β-phenoxyacetylamino-3chloromethyl -3-cephem-4carboxylate in 100 ml of dry THF, was dropwise added at −20° C. The resulting mixture was allowed to warm to room temperature in 0.5 hours. Water was added, and the mixture stirred for further 0.2 hours at room temperature. After the usual work-up and column chromatography, the title product was isolated in 65% yield.

Example 7 p-Methoxybenzyl 7β-phenoxyacetylamino-3-methylenecepham -4-carboxylate

To a solution of 48 ml of SmI$_2$ in THF (0.1M), a solution of 1.1 g of p-methoxybenzyl 7β-phenoxyacetylamino-3-chloromethyl-3-cephem-4carboxylate in 100 ml of dry THF, was added by dropping at −78° C. The resulting mixture was allowed to warm to room temperature in 0.5 hours. Water was added, and the mixture stirred for further 0.2 hours at room temperature. After the usual work-up and column chromatography, the title produce was isolated in 97% yield.

NMR (CDCl$_3$)δ ppm: 3.09 and 3.55 (2H, two d, J=13.8 Hz), 3.58 (2H, m), 3.79 (3H, s), 5.02 (1H, s), 5.05 (1H, s), 5.08 (1H, s), 5.14 (2H, s), 5.30 (1H, d, J=4.5 Hz), 5.61 (1H, dd, J=4.5 and 9.5 Hz), 6.18 (1H, d, J=9.5 Hz), 6.83-7.36 (9H, m).

Example 8 p-Methoxybenzyl 7β-phenoxyacetylamino-3-methylenecepham -4-carboxylate

Operating as in Example 7, but employing Cp$_2$Sm [prepared according to a known method starting from SmI$_2$ in THF(0.1M)] at room temperature instead of SmI$_2$ in THF (0.1M) at −78° C., the title compound was obtained in 60% yield.

We claim:

1. A process for preparing a compound of formula I

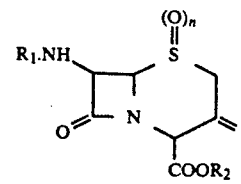

wherein n is 0 or 1, R$_1$ is hydrogen atom, linear or branched C$_1$-C$_5$ alkanoyl group; a benzoyl group, in which the phenyl ring is optionally substituted by one or more substituents chosen from: 1) C$_1$-C$_4$ linear or branched alkyl group, ii) NO$_2$, iii) C$_1$-C$_4$ linear or branched alkoxyl group, iv) a halogen atom; an optionally substituted, as defined above, phenyl-(linear or branched)-C$_2$-C$_4$-alkanoyl group; an optionally substituted, as defined above, phenoxy-(linear or branched)-C$_2$-C$_4$-alkanoyl group; a phthalimido group; a linear or branched C$_6$-C$_{10}$ thienylalkanoyl group; or linear or branched C$_4$-C$_8$ (1,3,4,-thiodiazolyl)thioalkanoyl residue: a linear or branched C$_1$-C$_4$ alkoxycarbonyl group; an optionally substituted, as defined above, phenoxycarbonyl group; an optionally substituted, as defined above, phenyl-(linear or branched)-C$_1$-C$_4$-alkoxycarbonyl group or a C$_1$-C$_4$ trihaloalkoxycarbonyl group, and R$_2$ is a carboxy protecting group chosen from linear or branched C$_1$-C$_4$ alkyl, a linear or branched C$_1$-C$_4$ trihaloalkyl group, and optionally substituted as defined above, benzyl, a trialkylsilyl, an optionally substituted, as defined above, diphenyl methyl, or a linear or branched C$_2$-C$_4$ alkenyl group, which process comprises reacting a compound of formula II

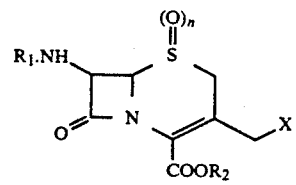

wherein X is halogen atom and R$_1$, n and R$_2$ are as defined above with a lanthanide complex chosen from samarium and ytterbium complexes, wherein the reaction is carried out in a solvent with up to 4 molar equivalents of the lanthanide complex at a temperature of from −100° C. to the solvent reflux temperature for a period of from a few minutes to one day and the resultant reaction mixture is quenched with a protic agent.

2. A process according to claim 1, in which the ligands of samarium and ytterbium complexes are chosen from halogenides, acetates and cyclopentadienyl group.

3. A process according to claim 1 in which the solvent is THF, dimethoxyethane, toluene, HMPA, acetonitrile, or a mixture thereof.

4. A process according to claim 1 in which the protic agent is water, methanol, ethanol, propanol, i-propanol, butanol, or t-butanol.

5. A process according to claim 1, in which the reaction is carried out at a temperature of from −78° C. to room temperature for a period of a few hours.

* * * * *